United States Patent [19]

Micinski

[11] Patent Number: 4,647,689

[45] Date of Patent: Mar. 3, 1987

[54] PREPARATION OF ALKYL TRIFLUOROACETOACETATE

[75] Inventor: Edward Micinski, Maryland Heights, Mo.

[73] Assignee: Monsanto Company, St. Louis, Mo.

[21] Appl. No.: 403,754

[22] Filed: Jul. 30, 1982

[51] Int. Cl.$^4$ .................... C07C 67/24; C07C 67/313; C07C 69/716

[52] U.S. Cl. .................................. 560/174; 560/184; 568/877

[58] Field of Search ....................... 560/184, 174, 178; 568/397, 404

[56] References Cited

FOREIGN PATENT DOCUMENTS 931689 7/1963 United Kingdom .

OTHER PUBLICATIONS

J.A.C.S., 65, pp. 389–392, (3–1943).
Ibid., 75, pp. 3152–3153, (7–1953).
Ibid., 69, pp. 1819–1820, (7–1947).
Tetrahedron, vol. 33, pp. 1637–1640, (1977).
Bergmann, et al., J. Chem. Soc., 1959, 3278–85.
Filler et al., Tetrahedron, 1963, vol. 19, pp. 879–889.

*Primary Examiner*—Vivian Garner
*Attorney, Agent, or Firm*—J. Timothy Keane; Stanley M. Tarter

[57] ABSTRACT

Alkyl trifluoroacetoacetates are prepared by acetylation of alkyl 3-alkoxy-3-hydroxy-4,4,4-trifluorobutanoates.

15 Claims, 1 Drawing Figure

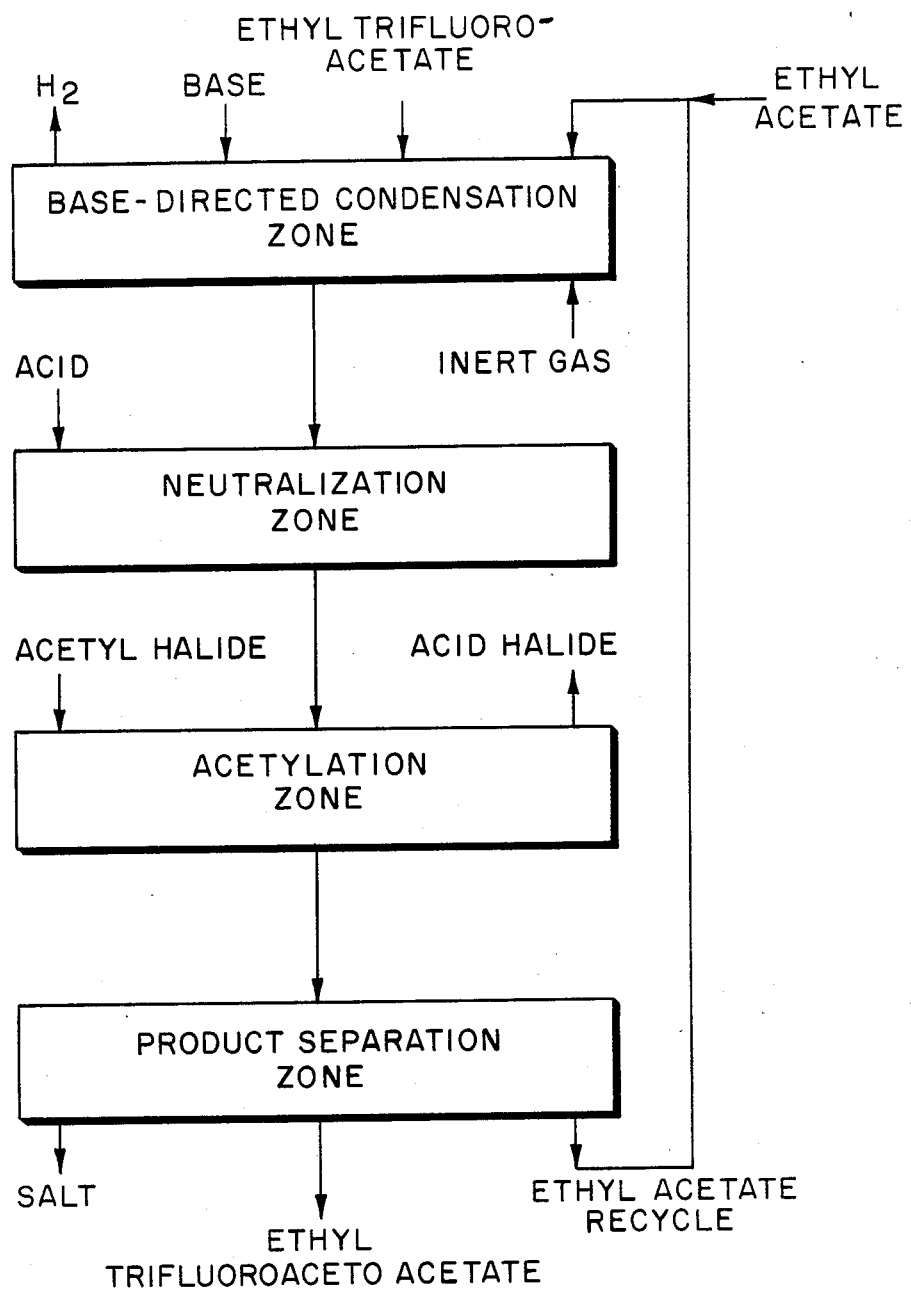

PREPARATION OF ALKYL TRIFLUOROACETOACETATE

The present invention provides the art with a novel and useful method of preparing alkyl trifluoroacetoacetate by means of acetylation of a lower alkyl 3-alkoxy-3-hydroxy-4,4,4-trifluorobutanoate.

It is well known in the prior art to link halogenated esters with other esters. For example, ethyl trifluoroacetoacetate has been prepared by an alkaline condensation of ethyl acetate with ethyl trifluoroacetate. Upon neutralization, a reaction product composed of a salt and the ethanol hemiketal of ethyl trifluoroacetoacetate is produced which is chemically identified as ethyl 3-ethoxy-3-hydroxy-4,4,4-trifluorobutanoate. To convert the hemiketal to ethyl trifluoroacetoacetate, the hemiketal is hydrolyzed with ethanol being removed. Unfortunately, this results in the formation of the hydrate of ethyl trifluoroacetoacetate. Also, ethanol is formed and discarded as a by-product, thus making the prior art procedure environmentally and economically unattractive.

Ethyl trifluoroacetoacetate is useful, as an intermediate for preparing agricultural chemicals and pharmaceuticals. To be best used as such it is usually necessary that the hydrate form be avoided. Accordingly, in such event the hydrate of ethyl trifluoroacetoacetate of the prior art must be dehydrated, which procedure entails an additional and expensive step. For example in accomplishing the dehydration, the prior art suggests employing cupric acetate to form a copper complex of the trifluoroacetoacetate. After filtration the complex is thereafter reacted with hydrogen sulfide to liberate trifluoroacetoacetate which is then isolated by distillation. In another prior art procedure, the trifluoroacetoacetate is isolated from the aqueous medium by solvent extraction and dehydration with dehydrating agents, for example, calcium chloride, magnesium sulfate and molecular sieves, with final product distillation.

The present invention provides for the convenient and economic preparation of anhydrous lower alkyl trifluoroacetoacetate. Furthermore, alkanols are not produced as a by-product. Instead, alkyl acetate is formed which can be recycled and used as a reactant to form additional alkyl trifluoroacetoacetate.

In accordance with the present invention, an alkyl 3-alkoxy-3-hydroxy-4,4,4-trifluorobutanoate is reacted with an acetylating agent, for example, acetyl halide or acetic acid anhydride to produce alkyl trifluoroacetoacetate and alkyl acetate. The resulting products are isolated one from the other. The recovered alkyl acetate can be conveniently recycled for condensation with additional alkyl trifluoroacetate to produce the alkyl 3-alkoxy-3-hydroxy-4,4,4-trifluorobutanoate. The halide may be fluoride, chloride, bromide, and iodide but preferably chloride. It can be seen that the more specific and preferred aspects of the present invention provide a method of preparing $C_1-C_5$ alkyl trifluoroacetoacetate by condensing in the presence of a strong base condensing agent $C_1-C_5$ alkyl acetate and $C_1-C_5$ alkyl trifluoroacetate. Strong bases used to prepare the condensation product include sodium metal, sodium ethoxide, sodium hydride and the like. The condensation product is neutralized with a strong, essentially anhydrous, mineral acid including hydrochloric acid, phosphoric acid, sulfuric acid and the like. Anhydrous hydrochloric acid is preferred. The neutralization product, which is alkyl 3-alkoxy-3-hydroxy-4,4,4-trifluorobutanoate (the $C_1-C_5$ alkanol hemiketal of $C_1-C_5$ alkyl trifluoroacetoacetate), is reacted with acetyl halide or acetic anhydride to produce $C_1-C_5$ alkyl trifluoroacetoacetate, $C_1-C_5$ alkyl acetate, hydrogen halide or acetic acid and the salt of the base and acid. Finally, the acetoacetate, the salt and the acetate are separated one from the other. The salt can be precipitated and removed by filtration, centrifugation, solvent extraction, etc. The acetoacetate, the hydrogen halide or acetic acid halide and the acetate are conveniently separated by fractional distillation or other suitable techniques.

In order to better illustrate the preferred method of the invention a flow diagram of the method is set forth in the accompanying drawing. At ambient temperature or other suitable reaction temperature an appropriate amount of a strong base, such as sodium hydride, preferably as an oil emulsion, is added to a base-directed condensation zone. Ethyl trifluoroacetate and ethyl acetate are then metered into the condensation zone and the reaction mixture stirred. A suitable inert organic solvent may also be added so that the reaction can be better controlled and separation of the final product can be facilitated. Suitable solvents include, for example, cyclohexane, dodecane ethyl ether, hexane, methyl cyclohexane, 1,2-dimethoxyethane, tetrahydrofuran, benzene, and the like. The condensation reaction is initiated in a controlled manner to form the sodium salt of ethyl trifluoroacetoacetate and ethanol. A nitrogen gas or other inert gas can be used to sweep and remove the evolved hydrogen gas.

The resulting reaction mixture is transferred to the neutralization zone where a strong anhydrous mineral acid, preferably anhydrous hydrochloric acid, is added, preferably at 10–15% molar excess to neutralize the reaction mixture and to form salt and the ethanol hemiketal of ethyl trifluoroacetoacetate. The product of neutralization is heated to remove excess hydrogen chloride as a gas.

Next, the product of neutralization is flowed into the acetylation zone where acetyl halide, preferably acetyl chloride, is reacted therewith to form hydrochloric acid, ethyl acetate and ethyl trifluoroacetoacetate.

The product of the acetylation step is transferred into the product separation zone. The salt precipitates and is filtered or otherwise separated. Ethyl acetate, ethyl trifluoroacetoacetate, and hydrogen chloride are separated one from the other by distillation or by other methods. Thus, ethyl trifluoroacetoacetate is produced as the final product along with ethyl acetate which may be recycled to the condensation zone.

An important aspect of the present invention is the acetylation of the product of the neutralization step. This product may be ethyl 3-ethoxy-3-hydroxy-4,4,4-trifluorobutanoate (ethanol hemiketal of ethyl trifluoroacetoacetate). It was found that upon conventional distillation of the product, the hemiketal decomposes to yield ethanol and ethyl trifluoroacetoacetate. Unfortunately, these two compounds co-distill and recombine in the distillation receiver to reproduce the hemiketal of ethyl trifluoroacetoacetate. Removal of essentially all of the ethanol is necessary in order to effectively chlorinate ethyl trifluoroacetoacetate to produce ethyl 2-chlorotrifluoroacetoacetate, a chemical found useful as an intermediate for making certain agricultural chemicals, viz., 2,4-disubstituted-5-thiazolecarboxylic acids and derivatives thereof, as disclosed in U.S. Pat. No. 4,199,506.

In the base-directed condensation step, one mole of ethyl trifluoroacetate results in the formation of one mole of ethanol. Therefore, approximately one mole of acetyl chloride is required per mole of ethyl trifluoroacetate in the acetylation step. However, it has been discovered that using slightly more than one equivalent of acetyl chloride results in an undesirable amount of the by-product, ethyl 3-acetoxy-4,4,4-trifluoro-2-butenoate. With 0.80 equivalent or less the amount of hemiketal in the product is undesirably high. Therefore, it is preferred that about 0.80 to 1.0 equivalent of acetyl chloride per equivalent of the hemiketal be used in the acetylation step. The use of about 0.95 equivalent of acetyl chloride minimizes formation of ethyl 3-acetoxy-4,4,4-trifluoro-2-butenoate while minimizing unreacted hemiketal in the distilled ethyl trifluoroacetoacetate.

The base-directed condensation is preferrably carried out in an inert organic medium. Such a medium is conveniently provided by the use of inert organic solvents with the selected alkyl acetate and the selected alkyl trifluoroacetate. Of the suitable solvents mentioned above, dodecane is the preferred solvent. Dodecane has a sufficiently high boiling point to provide excellent separation of the solvent from the acetoacetate final product in the distillation step. The amount of solvent employed is not critical as the use of a solvent can be avoided altogether. However, the reaction can be better controlled and the transfer of material from one zone to another is facilitated by using an organic solvent which is chemically inert in the process.

The acetylation reaction can be carried out at atmospheric pressure, although pressure employed is not critical. Thus, the pressure can be lower or higher than atmospheric, if needed to control the reaction or to maintain the reactants and product in the desired phase. The temperature at which the acetylation reaction is conducted is not of critical importance. Depending on the particular alkyl trifluorobutanoate and the pressure selected, the temperature at which the butanoate and acetyl halide are brought into reacting contact may range from about 10° C. to 115° C. or higher.

In regard to the preferred reaction conditions in the acetylation step, it should be borne in mind that the reaction of acetyl chloride with ethanol is exothermic. Normally, the reaction mixture is best maintained below 30° C. during the initial stage of the reaction during the addition of acetyl chloride. At this temperature the reaction rate, as indicated by the evolution of hydrogen chloride, is relatively slow. With an increase in reaction temperature, the rate of hydrogen chloride evolution may become undesirably high. In addition, significant losses of volatile materials may occur due to entrainment thereof in the hydrogen chloride upon rapid increases in temperature. On the other hand, if the reaction mixture is held at 30° C. or below, the rate of reaction may be unacceptably slow. Consequently, the mixture is gradually heated to reflux to achieve a controlled and acceptable rate of hydrogen chloride evolution.

By "lower alkyl" or "alkoxy" it is meant an alkyl moiety either straight or branched chain having 1-5 carbon atoms, including methyl, ethyl, n-propyl, isopropyl, methoxy, ethoxy, etc.

The following examples are presented for illustrative purposes only and are not intended as a restriction of the scope of the invention. All parts are given by weight unless otherwise designated.

EXAMPLE 1

Condensation

A dry reactor equipped with a heat exchanger, agitator, thermocouple, a cooled reflux condenser and mass flow meter was charged with 22.3 parts of sodium hydride (60% mineral oil dispersion) under a nitrogen blanket. The flow of nitrogen was minimized to reduce volatility losses. With stirring, 61.8 parts of dry cyclohexane was added as an inert organic solvent at room temperature to the sodium hydride oil dispersion. The stirred contents were then continuously charged via subsurface with 79.0 parts of ethyl trifluoroacetate over a 15 minute period. The stirred slurry was then heated to reflux at an atmospheric pressure to reflux. A Claisen condensation reaction was then initiated by slowly and continuously adding 53.9 parts of ethyl acetate at a steady rate over a period of 2 hours. The reaction rate was controlled by maintaining the reaction temperature between 45°-60° C.

After completion of the reaction as indicated by the cessation of the hydrogen evolution, an additional 55.7 parts of cyclohexane was added to the reaction mixture containing ethanol and the sodium salt of ethyl trifluoroacetoacetate to dilute the mixture.

Neutralization

The reaction mixture was transferred to a neutralization vessel made up of a reactor fitted with an agitator, a thermocouple and a cooled reflux condensor. After cooling the reaction mixture to 25°-30° C., anhydrous HCl (22.3 parts) was added via subsurface over a period of one hour. Throughout the HCl addition, the pot temperature was maintained below 30° C. The resulting slurry was then heated to reflux at atmospheric pressure and maintained at reflux to drive off excess HCl which was vented to a caustic scrubber.

Acetylation

The slurry was cooled to 25°-30° C. and 41.5 parts of acetyl chloride was slowly and continuously added over about 35 minutes, while the temperature of the mixture was kept below 30° C. The mixture thereafter was gradually heated to reflux at atmospheric pressure and maintained at reflux for about 1¾ hours, while approximately 20 parts of HCl evolved.

Product Separation

The slurry was maintained at 30° C. and filtered to remove precipitated sodium chloride. The resulting salt filter cake was washed twice with a total of 86.6 parts of cyclohexane. The wash filtrates were combined with the original ethyl trifluoroacetoacetate-containing filtrate and the combined material was transferred to a distillation vessel.

The distillation vessel was equipped with a fractionating column, a coiled condenser and a product receiver. Cyclohexane and ethyl acetate were distilled at 325 mm of Hg absolute and a vapor temperature ranging from 46°-71° C. This forecut contained ethyl acetate, which was recycled in subsequent production. Distillation of the second fraction proceeded at an initial pressure of 325 mm of Hg absolute and a vapor temperature of 71° C. and was terminated at a final pot temperature of 150°-160° C. at 20 mm of Hg absolute. This second fraction (approximately 82 parts) assayed at 94.0 weight percent of ethyl trifluoroacetoacetate. The yield of ethyl trifluoroacetoacetate was approximately 75%.

EXAMPLE 2

The example describes the use of dodecane instead of cyclohexane as the inert organic solvent. Also, the salt formed during the neutralization step is removed from the dodecane by aqueous extraction after ethyl acetate and ethyl trifluoroacetoacetate have been fractionally distilled.

The reactor as described in Example I was charged with 22 parts of sodium hydride (60% mineral oil dispersion) under a nitrogen blanket. With stirring 164 parts of dry dodecane was added at room temperature to the sodium hydride oil dispersion. The stirred contents were then continuously charged via subsurface with 74 parts of ethyl trifluoroacetate over a 15 minute period. The stirred slurry was then heated to 70° C. A Claisen condensation reaction was then initiated by slowly and continuously adding 51 parts of ethyl acetate at a steady rate over a period of 2 hours.

After completion of the condensation reaction, anhydrous HCl (21.9 parts) was added via subsurface over a period of one hour. Throughout the HCl addition, the pot temperature was maintained below 40° C. The resulting slurry was then heated to reflux at atmospheric pressure to drive off excess HCl.

The slurry was cooled to 58°-60° C. and 40 parts of acetyl chloride was continuously added via subsurface over one hour while maintaining a 58°-60° C. pot temperature. The mixture was gradually heated to reflux at atmospheric pressure and maintained at these conditions to drive off excess HCl. The temperature was then reduced to 75°-80° C. and the mixture was transferred to a distillation vessel equipped with a fractionating column and a cooled condenser and receiver. The distillation system was gradually evacuated to 315-320 mm of Hg absolute. At this pressure the mixture was heated to reflux to establish equilibrium in the column. The ethyl acetate forecut was then distilled and collected in a cooled receiver. Throughout the distillation the pot temperature gradually was increased. When the vapor temperature reached 75° C. (approximately 51 parts distillate being collected), the forecut receiver was isolated and drained into a container. This forecut was recycled. Distillation of the second fraction proceeded at an initial pressure of 315-320 mm Hg absolute and the pressure was rapidly decreased during the distillation of this fraction to a final pressure of 40 mm Hg absolute. The final pot temperature was 130° C. The yield of ethyl trifluoroacetoacetate in the second cut was about 80%.

The distillation pot residue was washed with 209 parts of water with agitation. The mixture was allowed to separate into an aqueous layer and an organic layer. The aqueous layer containing the sodium chloride was drained and sent to waste. A second water extraction was carried out in a similar manner. The organic layer containing the dodecane was purified for reuse by distillation.

EXAMPLE 3

This example illustrates the preparation of ethyl trifluoroacetoacetate wherein sodium ethoxide is the strong base used to condense ethyl acetate and ethyl trifluoroacetate.

A suitable flask was charged with 71.05 parts of ethyl trifluoroacetate and 57.33 parts of ethyl acetate. With rapid stirring, 34.04 parts of sodium ethoxide was added slowly so as to keep the raction mass below 35° C. The mixture was heated at reflux at atmospheric pressure for two hours. The reaction mixture was cooled to room temperature and was neutralized with 21 parts of anhydrous hydrochloric acid with the temperature being maintained below 40° C. Sodium chloride precipitated during the neutralization. Next, the pressure in the flask was reduced to 100 mm Hg absolute to remove unreacted hydrochloric acid. Next, 78.5 parts of acetyl chloride was added dropwise over a one hour period to the reaction mixture. After complete addition of the acetyl chloride the pressure was reduced to 100 mm of Hg absolute to remove the hydrogen chloride formed during the acetylation reaction. The resulting product was fractionally distilled at reduced pressure. An analysis of the distillation product showed an ethyl trifluoroacetoacetate yield of 59%. No hemiketal was present in the distillation product as determined by $^{19}F$ NMR.

EXAMPLE 4

This example illustrates the preparation of n-butyl trifluoroacetoacetate.

An appropriate three neck flask was charged with 40 parts of n-butyl trifluoroacetate, 32 parts of n-butyl acetate, and 100 parts of dodecane. With stirring 5.9 parts of sodium metal was added to the reaction mixture. The temperature of the mixture gradually rose to 55° C. over a 20 minute period. The temperature was controlled at 55° C. for one hour using a cold water bath. Thereafter, the reaction mixture was heated to 85°-90° C. and held at this temperature for 75 minutes to assure completion of the reaction. Next, 23.5 parts of sulfuric acid (95-98%) was added dropwise to the reaction mixture with stirring. The temperature of the mixture was controlled at 25°-30° C. using a cold water bath. After addition of the sulfuric acid, 18 parts of acetyl chloride was added dropwise over a period of five minutes to the reaction mixture with the temperature being controlled at 25°-30° C. The resulting mixture was a slurry with sodium chloride. The volatiles were removed by straight takeover vacuum distillation. The distillate was fractionally distilled to produce 10 parts of n-butyl trifluoroacetoacetate, the chemical structure of which was confirmed by NMR techniques and elemental analysis.

Although this invention has been described with respect to specific embodiments, the details thereof are not to be construed as limitations, for it is apparent that various equivalents, changes and modifications may be made without departing from the spirit and scope thereof. It is understood that such equivalent embodiments are intended to be included herein.

What is claimed is:

1. A method of preparing a $C_1$-$C_5$ alkyl trifluoroacetoacetate by bringing an acetylating agent selected from the group consisting of acetyl halides and acetic anhydride into reacting contact with a $C_1$-$C_5$ alkyl 3-alkoxy-3-hydroxy-4,4,4-trifluorobutanoate under acetylating conditions of temperature and pressure effective to prepare said $C_1$-$C_5$ alkyl trifluoroacetoacetate, said temperature being in a range having a lower limit of about 10° C. and having an upper limit at a temperature at which refluxing occurs for a reaction mixture containing said acetylating agent and said $C_1$-$C_5$ alkyl 3-alkoxy-3-hydroxy-4,4,4-trifluorobutanoate.

2. A method of preparing ethyl trifluoroacetoacetate by bringing acetyl halide or acetic acid anhydride into reacting contact with ethyl 3-ethoxy-3-hydroxy-4,4,4-trifluorobutanoate under conditions of temperature and pressure effective to prepare said ethyl trifluoroacetoacetate, said temperature being in a range having a lower limit of about 10° C. and having an upper limit at a temperature at which refluxing occurs for a reaction mixture containing said acetyl halide or said acetic acid anhydride and said ethyl 3-ethoxy-3-hydroxy-4,4,4-trifluorobutanoate.

3. A method of preparing $C_1$–$C_5$ alkyl trifluoroacetoacetate by condensing in the presence of a strong base condensing agent $C_1$–$C_5$ alkyl acetate and $C_1$–$C_5$ alkyl trifluoroacetate; neutralizing the condensation product with a strong mineral acid to produce $C_1$–$C_5$ alkyl 3-alkoxy-3-hydroxy-4,4,4-trifluorobutanoate; reacting said butanoate with acetyl halide or acetic acid anhydride at a temperature of at least about 10° C. and at a pressure sufficient to maintain said butanoate and said acetyl halide or acetic acid anhydride in solution to produce $C_1$–$C_5$ alkyl trifluoroacetoacetate, $C_1$–$C_5$ alkyl acetate and the salt of the said base and acid; and separating the said acetoacetate, the said salt and the said acetate one from the other.

4. The method of claim 3 wherein the strong base is selected from the group consisting of sodium metal, sodium ethoxide, and sodium hydride.

5. The method of claim 4 wherein the strong mineral acid is selected from the group consisting of hydrochloric acid, phosphoric acid and sulfuric acid.

6. The method of claim 3 wherein the condensation takes place in an inert organic solvent.

7. The method of claim 6 wherein the solvent is cyclohexane or dodecane.

8. A method of preparing ethyl trifluoroacetoacetate by:
(a) bringing into reacting contact ethyl acetate and ethyl trifluoroacetate in the presence of a strong base condensing agent to produce a reaction mixture of the salt of ethyl trifluoroacetoacetate and ethanol with hydrogen gas being evolved and removed;
(b) neutralizing said reaction mixture with a strong dry mineral acid to produce ethyl 3-ethoxy-3-hydroxy-4,4,4-trifluorobutanoate and the salt of the acid and base;
(c) bringing the product of neutralization into reacting contact with acetyl halide under conditions of temperature and pressure effective to produce ethyl acetate and ethyl trifluoroacetoacetate, said temperature being in a range having a lower limit of about 10° C. and having an upper limit at a temperature at which refluxing occurs for a reaction mixture containing said acetyl halide and said product of neutralization; and
(d) separating the salt, ethyl acetate and ethyl trifluoroacetoacetate one from the other.

9. A method of preparing ethyl trifluoroacetoacetate by:
(a) in a base-directed condensation zone, bringing into reacting contact ethyl acetate and ethyl trifluoroacetate in the presence of a strong base condensing agent to produce a reaction mixture of the salt of ethyl trifluoroacetoacetate and ethanol with hydrogen gas being evolved and removed as a gas;
(b) in a neutralization zone, neutralizing said reaction mixture with anhydrous hydrochloric acid to produce ethyl 3-ethoxy-3-hydroxy-4,4,4-trifluorobutanoate and the salt of the acid and base;
(c) in an acetylation zone, bringing the product of neutralization into reacting contact with acetyl halide under conditions of temperature and pressure effective to produce ethyl acetate and ethyl trifluoroacetoacetate with acid halide being removed as a gas, said temperature being in a range having a lower limit of about 10° C. and having an upper limit at a temperature at which refluxing occurs for a reaction mixture containing said acetyl halide and said product of neutralization;
(d) in a separation zone, separating the salt, ethyl acetate and ethyl trifluoroacetoacetate one from the other; and
(e) recycling the ethyl acetate to the condensation zone.

10. A method of preparing ethyl trifluoroacetoacetate by:
(a) in a base-directed condensation zone, bringing into reacting contact ethyl acetate and ethyl trifluoroacetate in the presence of sodium hydride to produce a reaction mixture of the sodium salt of ethyl trifluoroacetoacetate and ethanol with hydrogen gas being evolved and swept out of the condensation zone by an inert gas;
(b) in a neutralization zone, neutralizing said reaction mixture with anhydrous hydrochloric acid to produce ethyl 3-ethoxy-3-hydroxy-4,4,4-trifluorobutanoate;
(c) in an acetylation zone, bringing the product of neutralization into reacting contact with acetyl chloride under conditions of temperature and pressure effective to produce ethyl acetate and ethyl trifluoroacetoacetate with HCl being removed as a gas, said temperature being in a range having a lower limit of about 10° C. and having an upper limit at a temperature at which refluxing occurs for a reaction mixture containing said acetyl chloride and said product of neutralization;
(d) in a separation zone, separating the salt by filtration or centrifugation and separating ethyl acetate and ethyl trifluoroacetoacetate by fractional distillation; and
(e) recycling the ethyl acetate to the condensation zone.

11. The method of claim 10 wherein the anhydrous hydrochloric acid is employed in stoichiometric excess of up to about 10–15%.

12. The method of claim 11 where acetyl chloride is employed in the amount of about 1.0–0.8 stoichiometric equivalent.

13. A method of preparing a $C_1$–$C_5$ alkyl trifluoroacetoacetate by refluxing an acetylating agent selected from the group consisting of acetyl halides and acetic anhydride and $C_1$–$C_5$ alkyl 3-alkoxy-3-hydroxy-4,4,4-trifluorobutanoate wherein said refluxing step is carried out after mixing of the acetylating agent and the $C_1$–$C_5$ alkyl 3-alkoxy-3-hydroxy-4,4,4-trifluorobutanoate under non-refluxing conditions.

14. A method of preparing ethyl trifluoroacetoacetate by refluxing an acetyl halide or acetic acid anhydride with ethyl 3-ethoxy-3-hydroxy-4,4,4-trifluorobutanoate wherein said refluxing step is carried out after mixing of the acetyl halide or acetic acid anhydride with ethyl 3-ethoxy-3-hydroxy-4,4,4-trifluorobutanoate under non-refluxing conditions.

15. A method of preparing n-butyl trifluoroacetoacetate by refluxing an acetyl halide or acetic acid anhydride with n-butyl 3-butoxy-3-hydroxy-4,4,4-trifluorobutanoate wherein said refluxing step is carried out after mixing of the acetyl halide or acetic acid anhydride with n-butyl 3-butoxy-3-hydroxy-4,4,4-trifluorobutanoate under non-refluxing conditions.

* * * * *